US007721733B2

(12) United States Patent
Hughes et al.

(10) Patent No.: US 7,721,733 B2
(45) Date of Patent: May 25, 2010

(54) PORTABLE LIQUID OXYGEN DELIVERY SYSTEM

(75) Inventors: Roy A. Hughes, Port Orange, FL (US); Jonathan C. McLellan, Harrison City, PA (US); Margaret McLellan, legal representative, Harrison City, PA (US); Douglas Whitcher, Woodstock, GA (US)

(73) Assignee: RIC Investments, LLC, Wilmington, DE (US)

( * ) Notice: Subject to any disclaimer, the term of this patent is extended or adjusted under 35 U.S.C. 154(b) by 972 days.

(21) Appl. No.: 11/493,151

(22) Filed: Jul. 26, 2006

(65) Prior Publication Data

US 2007/0039616 A1 Feb. 22, 2007

Related U.S. Application Data

(60) Provisional application No. 60/703,690, filed on Jul. 29, 2005.

(51) Int. Cl.
*A61M 11/00* (2006.01)

(52) U.S. Cl. ........................... 128/201.21; 128/DIG. 27

(58) Field of Classification Search .......... 128/DIG. 27, 128/201.21, 205.22; 62/50.1, 50.2, 48.1
See application file for complete search history.

(56) References Cited

U.S. PATENT DOCUMENTS

| | | | | |
|---|---|---|---|---|
| 3,864,928 | A * | 2/1975 | Eigenbrod | 62/48.1 |
| 4,625,753 | A | 12/1986 | Gustafson | |
| 4,956,975 | A | 9/1990 | Gustafson | |
| 5,228,585 | A | 7/1993 | Lutgen et al. | |
| 5,373,702 | A | 12/1994 | Kalet et al. | |
| 5,404,918 | A | 4/1995 | Gustafson | |
| 5,421,161 | A | 6/1995 | Gustafson | |
| 5,421,162 | A | 6/1995 | Gustafson et al. | |
| 5,572,875 | A | 11/1996 | Gustafson | |
| 5,893,275 | A | 4/1999 | Henry | |
| 6,128,908 | A | 10/2000 | Gustafson | |
| 6,393,847 | B1 | 5/2002 | Brooks et al. | |
| 6,651,659 | B2 | 11/2003 | Izuchukwu | |
| 6,742,517 | B1 | 6/2004 | Frye et al. | |
| 2002/0056451 | A1 * | 5/2002 | Frankie et al. | 128/201.21 |
| 2006/0219245 | A1 | 10/2006 | Holder | |

OTHER PUBLICATIONS

Respironics, Inc., "Many Questions About Liquid Oxygen", brochure.

Healthdyne Technologies, "Service Manual for Protégé Stationary Portable liquid oxygen units".

Nellcor Puritan Bennett Inc., "HELiOS H300 Personal Oxygen System Filling Guide", 2003.

* cited by examiner

*Primary Examiner*—Steven O Douglas
(74) *Attorney, Agent, or Firm*—Michael W. Haas

(57) ABSTRACT

A portable liquid oxygen medical delivery system including a portable liquid oxygen delivery apparatus and a portable liquid oxygen recharger. The portable liquid oxygen delivery apparatus contains an initial quantity of liquid oxygen. The liquid oxygen delivery apparatus is sufficiently lightweight for portability by an ambulatory patient and has a fill port for receiving liquid oxygen. The liquid oxygen recharger stores a supplemental quantity of liquid oxygen and is also sufficiently lightweight for portability by an ambulatory individual. The liquid oxygen recharger has an interface for interfacing the liquid oxygen recharger with the portable liquid oxygen delivery apparatus for delivering the supplemental quantity of liquid oxygen to the portable liquid oxygen delivery apparatus.

22 Claims, 5 Drawing Sheets

PORTABLE LIQUID OXYGEN DELIVERY SYSTEM

CROSS-REFERENCE TO RELATED APPLICATIONS

This application claims priority under 35 U.S.C. §119(e) from provisional U.S. patent application No. 60/703,690, filed Jul. 29, 2005, the contents of which are incorporated herein by reference.

BACKGROUND OF THE INVENTION

1. Field of Invention

The present invention relates generally to a liquid oxygen delivery system, and, more particularly, to a liquid oxygen delivery system that includes a portable recharger for providing supplemental liquid oxygen to a portable liquid oxygen delivery device for increasing the utilization capacity of the portable liquid oxygen delivery device.

2. Description of the Background Art

The delivery of supplemental oxygen to a patient is typically prescribed for individuals suffering from pulmonary/respiratory problems. The prescription and delivery of supplemental oxygen is undertaken to ensure that sufficient oxygen levels are received by the patient. Situations where supplemental oxygen may be prescribed include individuals afflicted with a chronic obstructive pulmonary disease, such as asthma, as well as individuals suffering from diseased or damaged lungs.

The delivery of supplemental oxygen may be provided utilizing one of three predominant methods. For non-ambulatory patients, or for use during the non-ambulatory period of an individual, oxygen may be provided from a stationary oxygen concentrator that generates oxygen from air, typically using a pressure swing absorption gas separation system. While suitable for their intended purpose, oxygen concentrators are generally ill-suited for portability due the relatively bulky and heavy gas compressor and sieve beds needed to generate a practical quantity of oxygen, and, therefore, are not intended for use with an ambulatory individual.

A second predominant oxygen delivery method is a compressed oxygen system in which the oxygen to be consumed by the user is compressed and stored in a high pressure storage vessel or tank. These storage vessels can be made small enough so as to be portable. Compressed gas storage systems are generally prescribed when the user does not need oxygen all the time, such as only when walking or performing physical activity. One disadvantage of compressed oxygen systems is that oxygen stored under pressure may create a hazard if the storage vessel is damaged, which can occur if it is dropped, bumped, punctured, etc. Also, small, portable oxygen tanks hold a relatively small amount of gas. Thus, they are limited in how long the oxygen inside the tank will last, which will depend on the prescribed flow rate and the type/size of the tank.

A third predominant oxygen delivery method, which is typically used as an alternative to compressed oxygen systems, is a liquid oxygen ("LOX") system. A conventional LOX system includes a large stationary LOX storage canister that is located at and remains at the user's home. The stationary LOX canister is replenished periodically from a mobile LOX storage vessels, which is typically a truck carrying a large quantity of LOX. The LOX system also includes a small, portable delivery apparatus weighing from five to thirteen pounds that can be filled from the stationary unit for trips outside the home. The portable delivery apparatus converts the liquid oxygen to a breathable gas for consumption by the user. These systems have limited utilization due to the low LOX capacity of the portable delivery apparatus and the administered LOX flow rate. Furthermore, even when not in use, the LOX within the portable delivery apparatus evaporates at a typical rate of one pound per day, empting the portable delivery apparatus LOX supply over time even if it is not used. Consequently, a disadvantage of a portable LOX system includes the requirement that the user must return home regularly, such as by the end of the day, to refill the portable delivery apparatus from the home stationary LOX storing canister.

One such LOX system is disclosed in U.S. Pat. No. 6,742,517 ("the '517 patent") entitled, High Efficiency Liquid Oxygen Storage and Delivery System. As disclosed in this patent, a typical LOX system includes a stationary LOX storage canister located in an individual's home and a portable LOX delivery unit that the patient uses outside the home. The stationary LOX storage canister must be periodically refilled with LOX by a distributor via a truck, van, or other vehicle capable of carrying a large quantity of liquid oxygen. The name of the portable delivery unit in the commercial implementation of this LOX system and described in the '517 patent is the HELiOS®. As identified at the HELiOS website, www.heliosoxygen.com, the HELiOS H300 portable LOX delivery unit has a limited capacity for storing liquid oxygen. This capacity is limited to eight to ten hours of usage, after which the LOX is depleted.

The HELiOS weighs approximately 3.6 pounds when completely filled with LOX, and approximately 2.75 pounds empty. The HELiOS portable unit is designed to be refilled from a stationary LOX storage canister and has a LOX capacity of 0.9 pounds. Because the typical evaporation of LOX is one pound per day, the LOX within the HELiOS unit will most likely evaporate during a day, even without the LOX being utilized by an individual. Furthermore, the evaporation of LOX can occur at a faster rate than one pound per day when the LOX canister is actually being worn by an ambulatory patient, because the movement of the patient increases the friction within the LOX canister, thus elevating the temperature of the LOX and expediting the evaporation of the LOX.

While portable LOX systems are suitable for their intended purposes, they nonetheless have a significant drawback, namely their limited LOX capacity. Current portable LOX systems provide an individual with only a short time of LOX availability. Hence, the ambulatory patient is, in effect, tethered to their home because they must remain within close proximity of the home in order to have access to their LOX supply for refilling the portable LOX system. As noted with respect to the HELiOS, it only has a capacity of eight to ten hours, which is not typically sufficient for a fairly active individual who also works.

One solution to extend the time away from home by an ambulatory LOX patient consists of incorporating a standard stationary (home) LOX storage unit into an automobile for subsequent refilling of the portable LOX device. This solution requires retrofitting an automobile to accommodate the large liquid oxygen tank. Such LOX tanks are very large, bulky, and extremely heavy, weighing over a hundred and ten pounds. Such arcane measures of retrofitting an automobile are expensive, and typically require a large automobile such as a truck or SUV. Thus, retrofitting is not practical for most individuals and also limits the overall mobility of an individual, as they must ensure that they are either located close to home or near their respective retrofitted automobile.

For those individuals who have not retrofitted their vehicle, traveling even small distances is a problem. For instance, because the provision of liquid oxygen for therapeutic purposes requires a prescription, the refilling of a portable device cannot typically be done if travel occurs across state lines. Hence, a problem arises for people utilizing prescription oxygen when they travel among states. They must consider how long they can travel between portable refills, and how can the refill be accomplished.

SUMMARY OF THE INVENTION

Accordingly, there is a need for a liquid oxygen delivery system that overcomes the shortcomings of conventional, i.e., enables an individual to utilize a portable LOX delivery device for an extended period of time. Such a system must have a sufficient capacity to provide a user with a quantity of LOX for inhalation during that period of time, in addition to accounting for the loss of LOX due to its natural evaporation. This object is achieved according to one embodiment of the present invention by providing a portable liquid oxygen delivery system that includes a portable liquid oxygen delivery apparatus and a portable liquid oxygen recharger. The portable liquid oxygen delivery apparatus has an interior for containing an initial quantity of liquid oxygen. The liquid oxygen delivery apparatus is sufficiently lightweight for portability by an ambulatory patient and has a fill port for receiving liquid oxygen into the interior. The liquid oxygen recharger has an interior for storing a supplemental quantity of liquid oxygen and is sufficiently lightweight for portability by an ambulatory individual.

The liquid oxygen recharger has an interface for interfacing the liquid oxygen recharger with a stationary (home) liquid oxygen storage canister for receiving liquid oxygen from the stationary liquid oxygen storage canister. Additionally, the liquid oxygen recharger has an interface for interfacing the liquid oxygen recharger with the portable liquid oxygen delivery apparatus for delivering the supplemental quantity of liquid oxygen into the interior of the portable liquid oxygen recharger. Hence, an ambulatory patient is provided with a liquid oxygen from the portable liquid oxygen delivery apparatus. The portable liquid oxygen delivery apparatus is then recharged with a supplemental quantity of liquid oxygen from the portable liquid oxygen recharger.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of “a”, “an”, and “the” include plural referents unless the context clearly dictates otherwise.

DESCRIPTION OF THE PREFERRED EMBODIMENT

Figure 1:
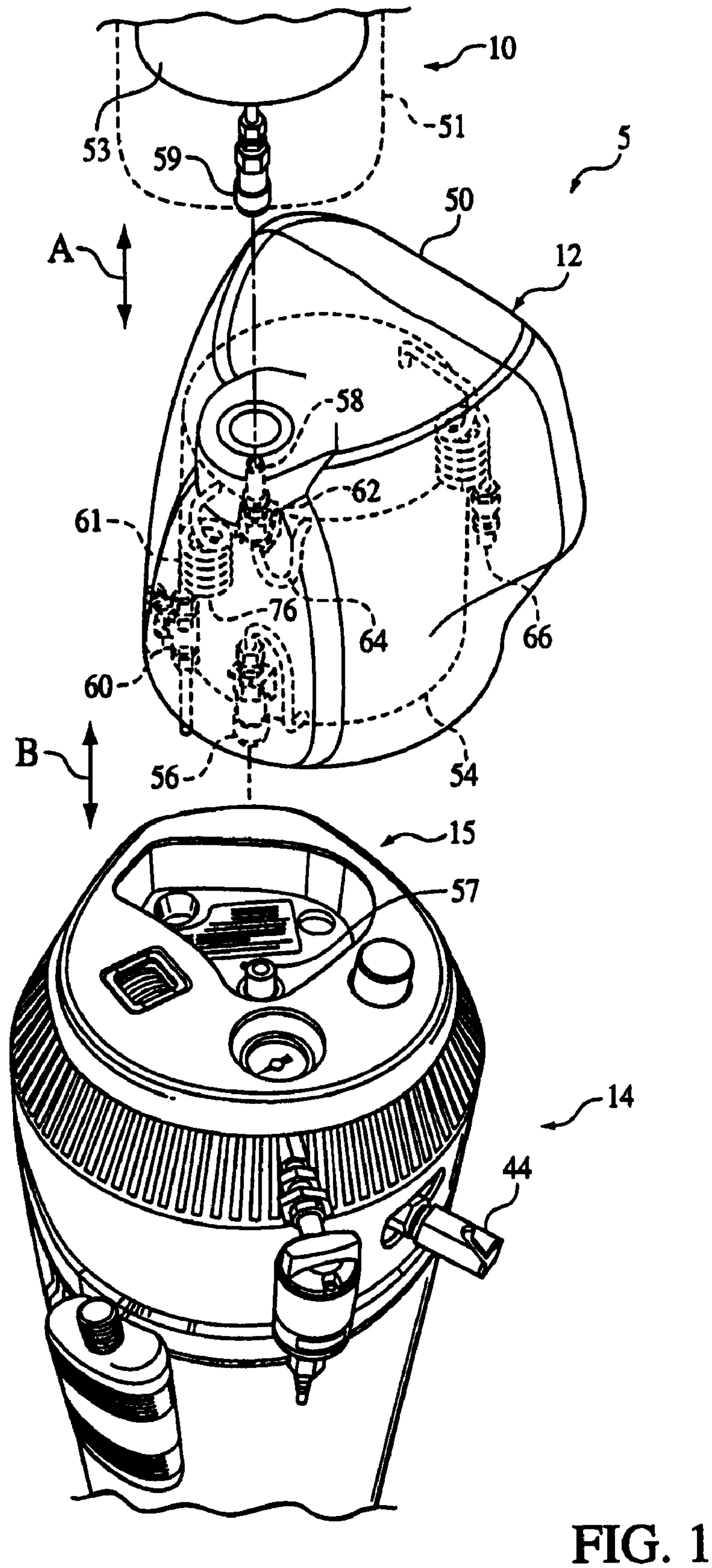
FIG. 1 illustrates a portable liquid oxygen recharging system according to the principles of the present invention.

As shown in FIG. 1, a portable liquid oxygen recharging system 5 for an individual according to the principles of the present invention, includes a portable liquid oxygen (LOX) delivery apparatus 10, a portable LOX recharger 12, and a stationary LOX storage canister 14. The stationary LOX storage canister is installed in the user’s home or residence, while portable LOX delivery apparatus 10 and portable LOX recharger 12 are designed to be easily transported by the user away from the stationary LOX storage canister. Portable LOX delivery apparatus 10 is connectable to LOX recharger 12 or to stationary LOX storage canister 14 to receive liquid oxygen from the LOX recharger or the stationary LOX storage canister. LOX recharger 12 is connectable to the stationary LOX storage canister to receive liquid oxygen from the stationary LOX storage canister. The coupling of portable LOX delivery apparatus 10 to LOX recharger 12 is illustrated by arrow A, and the coupling of LOX recharger 12 to stationary LOX storage canister 14 is illustrated by arrow B.

It should be noted that FIG. 1 illustrates a conventional stationary LOX storage canister 14, including a conventional interface, generally indicated at 15, for coupling LOX recharger or portable LOX delivery apparatus to the LOX storage canister. It can be appreciated that the specific configuration for the a stationary LOX storage canister and/or interface 15 suitable for use with the portable LOX recharger of the present invention can deviate from than shown. Of course, the physical arrangement for the stationary LOX storage canister, its interface, portable LOX recharger 14, and its interface, can vary so long as the function of enabling the portable LOX recharger to operatively couple to the stationary LOX storage container is achieved.

In operation, portable LOX delivery apparatus 10 is typically provided an initial charge of LOX from stationary LOX storage canister 14. Portable LOX recharger 12 also receives a charge of LOX from stationary LOX storage canister 14. During subsequent utilization of the stored LOX from portable LOX delivery apparatus 10, liquid oxygen from LOX recharger 12, which is also fully portable, is used to recharge portable LOX delivery apparatus 10. Thus, the LOX recharger provides a portable, secondary source of LOX, hence providing portable LOX delivery apparatus 10 with an extended operational duration. As a result, the user need not return portable LOX delivery apparatus 10 to stationary LOX storage canister 14 in order to recharge the portable LOX delivery apparatus, as is required by conventional LOX systems.

The present invention also contemplates that LOX storage container 14 can be replaced by or used in combination with a home liquid oxygen generating system, which is typically referred to as a liquefaction system. An example of such a liquefaction system is described in U.S. Pat. No. 5,893,275, the contents of which are incorporated herein by reference.

Figure 2:
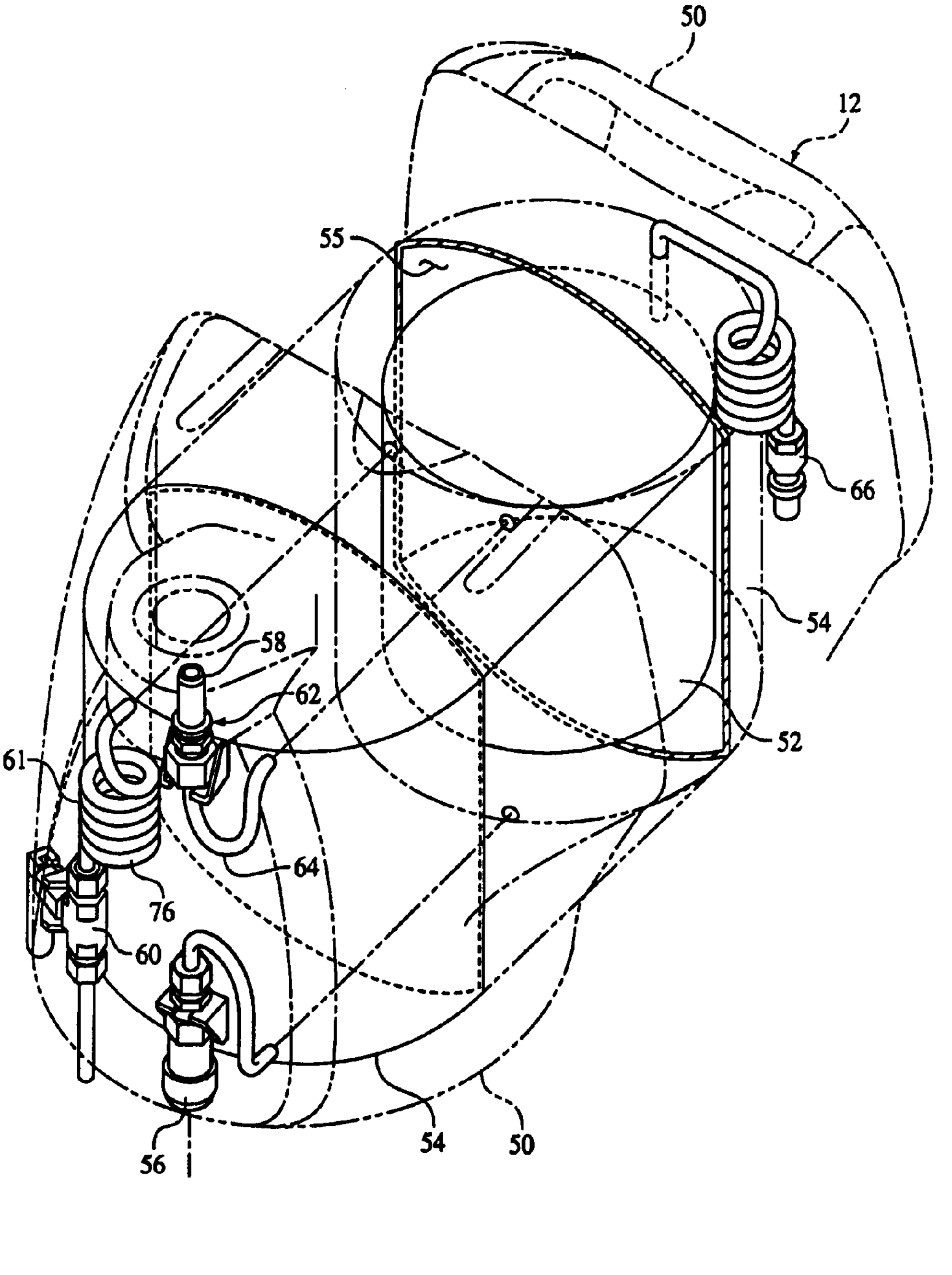
FIG. 2 illustrates the internal features of the portable liquid oxygen recharger of FIG. 1.
Figure 3:
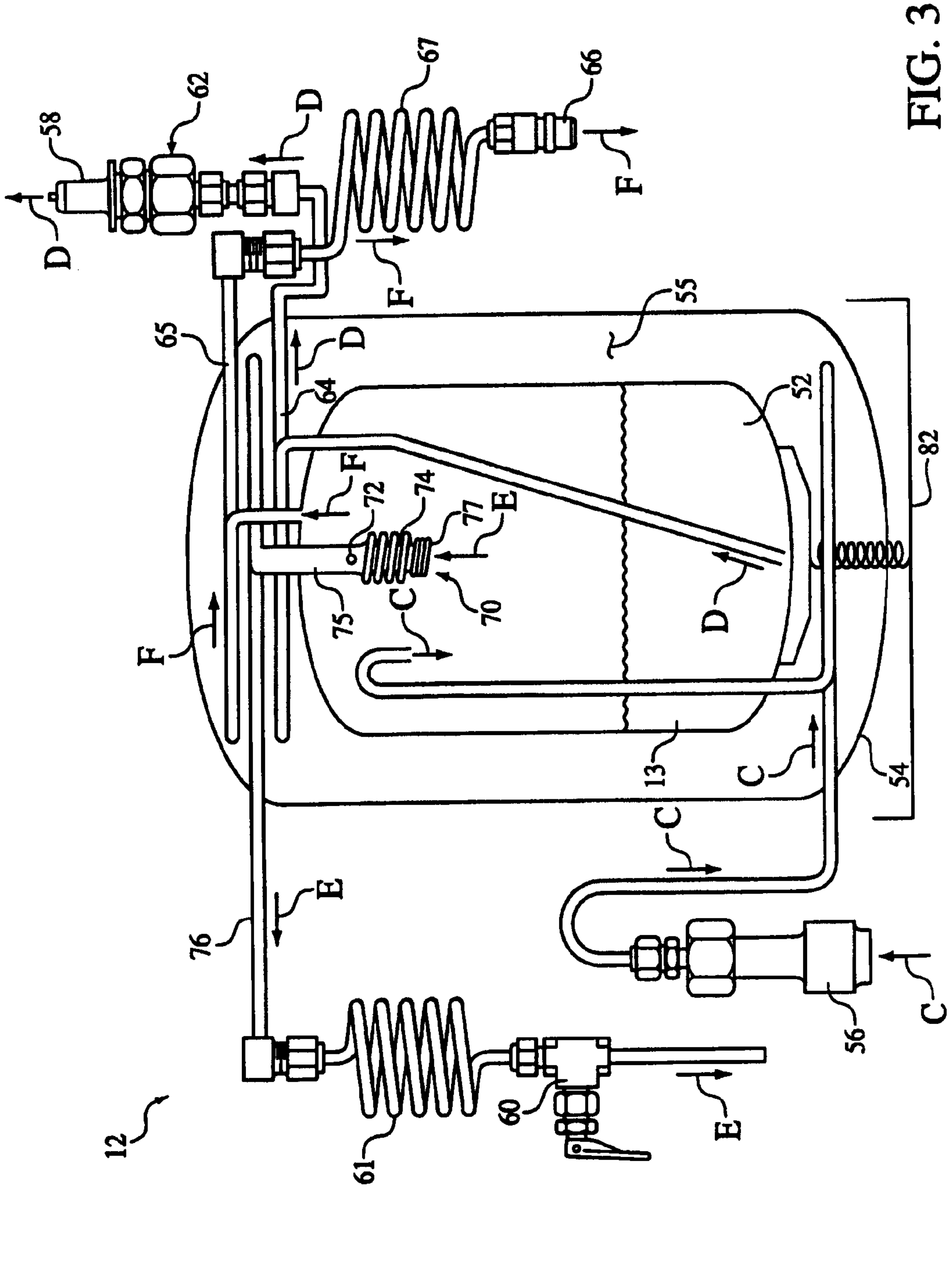
FIG. 3 schematically illustrates the portable liquid oxygen recharger of FIG. 1.

As shown in FIGS. 1-3, portable LOX recharger 12 includes a general housing 50 and stores LOX within the housing. Inside housing 50, is an inner recharger LOX container 52, which is spaced from an outer recharger LOX container 54. In an exemplary embodiment, a space 55 between outer container 54 and inner container 52 is evacuated to at least a partial vacuum in order to minimize heat transfer to inner LOX container 52. Portable LOX recharger 12 includes a fill port 56 in communication with inner container 52, enabling the transfer of LOX from stationary LOX storage canister 14, e.g., located at home, into inner container 52 of the portable LOX recharger 12. The transfer or filling of container 52 with LOX 13 via fill port 56 is illustrated by arrows C in FIG. 3. Fill port 56 is adapted for mating engagement with a discharge port 57 of stationary LOX storage canister 14. Mating engagement may be via a direct connection or via a transfer conduit (not shown). It is to be understood that any connection assembly for joining the fill port and the discharge port are contemplated by the present invention.

Portable LOX recharger 12 includes a portable LOX recharger dispensing assembly 62 that is used to transfer LOX from within inner container 52 to portable LOX delivery apparatus 10. Dispensing assembly 62 includes a discharge port 58 in communication with inner container 52 via a discharge tube 64 one end of which is disposed at a bottom (lower) portion of the inner container, enabling LOX 13 to be transferred from portable LOX recharger 12 to portable LOX delivery apparatus 10. The discharge or transfer of LOX 13 from container 52 via discharge port 58 is illustrated by arrows D in FIG. 3.

Discharge port 58 is adapted for mating engagement with a fill port 59 of portable LOX delivery apparatus 10. Mating engagement may be via a direct connection or via a transfer conduit (not shown). It is to be understood that any connection assembly for joining discharge port 58 and fill port 59 are contemplated by the present invention. Fill port 59 in portable LOX delivery apparatus 10 communicates the LOX to a storage dewer 53 housed in the portable LOX delivery apparatus. A housing 51 of portable LOX delivery apparatus 10 is illustrated by dashed lines in FIG. 1. It is to be understood that the present invention contemplates using any suitable technique for transforming the liquid oxygen to a gas suitable for consumption by the user. It is to be further understood that the present invention contemplates using any suitable device or technique for interfacing the flow of gas with an airway of patient, including a nasal cannula or a mask.

A portable LOX recharger filling vent 60 also communicates with portable LOX recharger's 12 inner container 52 via a vent tube 76. Filling vent 60 is provided to communicate inner container 52 with the ambient atmosphere outside the portable LOX recharger. Normally, recharger filling vent 60 is closed, preventing the inner container from communicating with the ambient atmosphere. However, when portable LOX recharger 12 is being filled with LOX, recharger filling vent 60 is opened to relieve internal pressure within inner container 52, as indicated by arrows E. This is done to enable LOX to flow from stationary LOX storage canister 14 into portable LOX recharger's 12 inner container 52. A boil-off coil 61 is provided to allow LOX traveling in vent tube 76 to heat, thereby converting it to a gas before being discharged to ambient atmosphere.

An automatic shutoff assembly 70 is provided in container 52 so that it is utilized during the transfer of LOX from stationary LOX storage canister 14 into inner container 52 of portable LOX recharger 12, i.e., when recharger filling vent 60 is open. Automatic shutoff assembly 70 includes an internal pressure release tube 75, a pressure equalizing aperture 72, a floating shutoff plug 74, and a floating shutoff plug holder 77. Internal pressure release tube 75 communicates with vent tube 76 and inner container 52, so that internal pressure in inner container 52 may escape from the inner container through the opening of internal pressure release tube 75 and into vent tube 76. The internal pressure eventually escapes to the ambient atmosphere through open recharger filling vent 60.

Floating shutoff plug holder 77 positions floating shutoff plug 74 a predetermined distance from an opening (not shown) of internal pressure release tube 75, so that internal pressure may escape through the internal pressure release tube 75 as LOX is filled into inner container 52. Floating shutoff plug holder 77 is situated to allow floating shutoff plug 74 to move freely between the opening of the internal pressure release tube 75 and the predetermined distance. As the level of LOX 13 in inner container 52 reaches a maximum capacity, the floating shutoff plug 74 is lifted by the LOX toward the opening of the internal pressure release tube 75, i.e., plug 74 floats on the LOX and, in combination with internal pressure release tube 75, operates as a float valve.

Floating shutoff plug 74 is of an adequate size so that once the floating shutoff plug 74 engages the opening of the internal pressure release tube 75, the floating shutoff plug 74 effectively prevents LOX from escaping to the ambient atmosphere through tubes 75 and 76. Pressure equalizing aperture 72 communicates between an interior or internal pressure release tube 75 and inner container 52. The size of pressure equalizing aperture 72 is substantially smaller than the opening of internal pressure release tube 75. Accordingly, pressure equalizing aperture 72 permits only a nominal amount of gas or LOX to flow from inner container 52 to vent tube 76.

Pressure equalizing aperture 72 is situated on a side of the internal pressure release tube 75, so that pressure equalizing aperture 72 always remains open even after a floating shutoff plug 74 closes the opening of internal pressure release tube 75. Because of its smaller size, pressure equalizing aperture 72 emits a distinct and audibly different sound than any sound associated with the opening of internal pressure release tube 75 when internal pressure or LOX passes through aperture 72. In other words, before plug 74 seals tube 75 little or no sounds is made by gas (or LOX) passing into tube 75 through the opening at the bottom of tube 75. After plug 74 seals the opening to tube 75, gas or LOX can pass from inner container 52 into tube 75 through aperture 72. However, this will cause a distinct sound, such as a whistle or hum, due to the gas or LOX passing through aperture 72.

Such a distinct sound alerts a patient that portable LOX recharger 12 is full. This automatic alert feature helps to reduce the amount of gas or LOX released into the ambient atmosphere through recharger filling vent 60 when the recharger filling vent is open. Further, pressure equalizing aperture 72 assists in equalizing the pressure inside and outside inner container 52. As the pressure inside inner container 52 approaches the pressure outside inner container 52, floating shutoff plug 74 shifts from the opening of internal pressure release tube 75 to the predetermined distance, thus preventing floating shutoff plug 74 from perpetually blocking the opening of internal pressure release tube 75.

A pressure relief valve 66 is also in communication with inner container 52 of the portable LOX recharger 12 via a pressure relief tube 65. In the event that pressure within the inner container 52 exceeds a predetermined limit, for example due to the evaporation of the LOX, pressure relief valve 66 opens venting gas to the ambient atmosphere. The venting of gas for the purpose of relieving excess pressure in container 52 is indicated by arrows F in FIG. 3. Pressure relief tube 65 includes a boil-off portion 67 to heat the LOX in tube 65 so that it transitions to a gas prior to being discharged to the ambient atmosphere.

As shown in FIGS. 1 and 2, the present invention contemplates providing fill port 56 at the bottom of housing 50. This configuration allows portable LOX recharger 12 to be placed on top of stationary LOX storage canister 14 during filling. It is to be understood that the portable LOX recharger 12 and/or stationary LOX storage canister 14 can include features for attaching the LOX recharger to the stationary LOX storage canister, such as clamps, interlocking members, and any other configuration suitable to ensure a secure fit between these two components.

Similarly, the present invention contemplates providing discharge port 58 at the top of housing 50. This configuration allows portable liquid oxygen (LOX) delivery apparatus 10 to be placed on top of portable LOX recharger 12 during filling. It is to be understood that portable LOX recharger 10 and/or LOX recharger 12 can include features for attaching the LOX recharger 12 to the portable LOX delivery apparatus 10, such as clamps, interlocking members, and any other configuration suitable to ensure a secure fit between these two components. It is to be further understood that the present invention contemplate other arrangements, configurations, and locations for fill port 56 and discharge port 58. For example, both ports can be provided on the side of the housing, recessed within the housing, covered by an access panel, or any combination thereof.

Portable LOX recharger 12 preferably has a LOX capacity of two liquid liters and weighs approximately five pounds when empty and ten pounds when filled with LOX. The conventional portable HELiOS H300 portable LOX delivery storage/delivery device has a LOX capacity of zero point nine (0.9) pounds. Because a typical LOX system loses approximately one pound of LOX per day due to evaporation, this conventional system lacks the capacity for extended usage, as its initial capacity of LOX is less than that which would typically evaporate in a single day. Accordingly, it is a feature of the present invention that portable LOX recharger 12 has a capacity at least equal to the capacity of portable LOX delivery apparatus 10 plus an evaporation compensation quantity of one pound of LOX.

One pound of LOX is equivalent to zero point four (0.4) liters of LOX. Accordingly, the preferred embodiment has a capacity of approximately two liters of LOX weighing five pounds. With a normal loss rate of one pound per day and a utilization rate of zero point nine (0.9) pounds per eight hours, portable LOX recharger 12 provides approximately twenty-seven hours of LOX utilization by an individual over a two day period, with an additional quantity to compensate for normal LOX evaporation over the two day period, without requiring the individual to return home for refilling of the portable LOX delivery apparatus 10 by stationary LOX storage canister 14. This invention enables an ambulatory patient to conveniently engage in an overnight business trip or other excursion.

Figure 4:
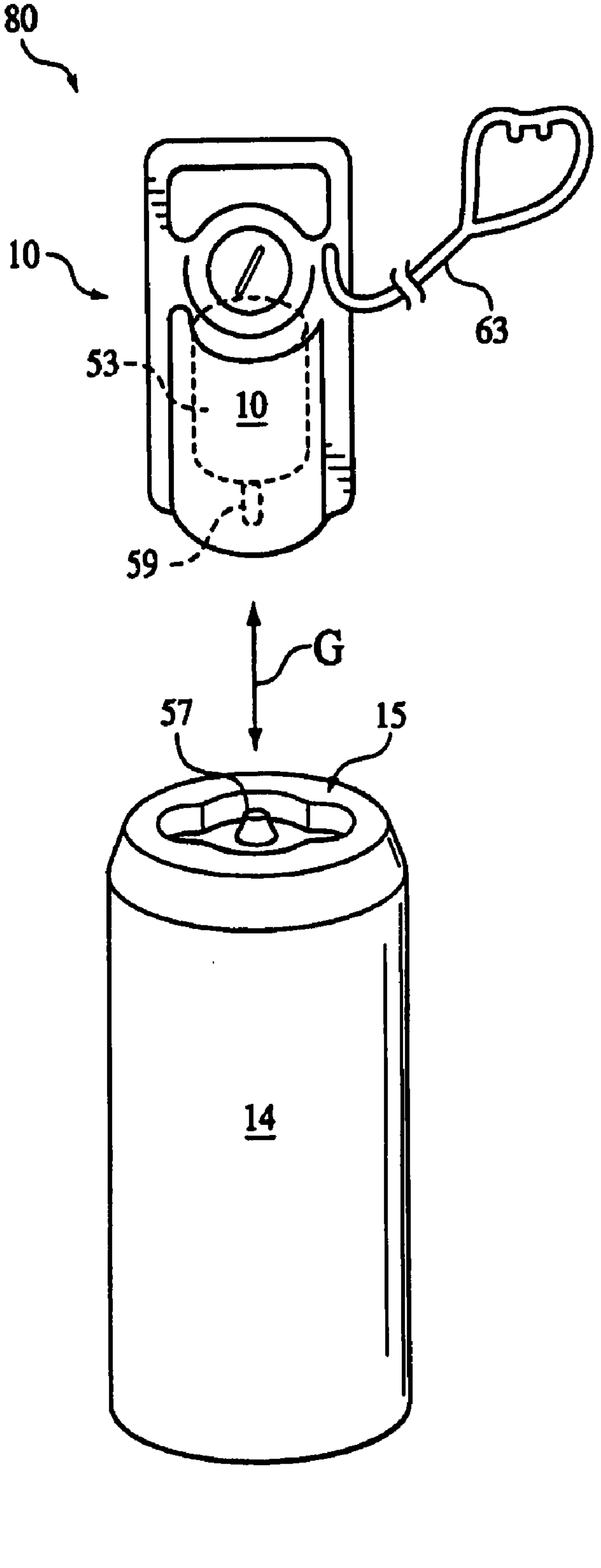
FIG. 4 (PRIOR ART)
FIG. 4 schematically illustrates a conventional LOX system, including a large LOX storage tank and a portable LOX delivery apparatus.

FIG. 4 illustrates the conventional LOX system 80, which includes a stationary (non-portable) storage canister 14 and portable LOX delivery apparatus 10. Stationary LOX storage canister 14 is of standard dimensions, which typically holds from twenty to sixty or more liters of LOX. A stationary LOX storage canister holding thirty-six liters of LOX weighs approximately eighty-five pounds, while a stationary LOX storage canister containing forty-three liters of LOX weighs about one hundred and ten pounds.

Stationary LOX storage canister 14 generally includes a primary reservoir container assembly, a main LOX transfer connector, a main-unit oxygen gas transfer connector, and a main-unit primary relief valve. The primary reservoir container assembly includes an outer container, an inner primary reservoir LOX container spaced apart from the outer container, and insulation between the inner and outer containers. The space between the outer container and the inner container is preferably evacuated to at least a partial vacuum in order to minimize heat transfer to the LOX inside the inner container.

For filling, stationary LOX storage canister 14, a fill port 44 is provided that communicates with the inner primary reservoir LOX container. A discharge port 57 also in communication with inner primary reservoir LOX container enables LOX to be discharged for filling portable LOX delivery apparatus 10.

Portable LOX delivery apparatus 10 is smaller and lighter than stationary LOX storage canister 14. Portable LOX delivery apparatus 10 weighs approximately three point six pounds when fully charged with LOX and approximately two point seven pounds when empty. Portable LOX delivery apparatus 10 includes a portable delivery apparatus LOX container 53, a portable delivery apparatus LOX transfer connector, a fill port 59, a LOX withdrawal conduit, LOX warming coil, and a relief valve. A cannula 63 connects to an outlet of the portable LOX delivery apparatus for communicating a flow of gas to an airway of a user. To fill portable LOX delivery apparatus 10, the user mounts the portable LOX delivery apparatus on stationary LOX storage canister 14, as indicated by arrow G, such that fill port 59 is coupled to discharge port 57.

Portable LOX delivery apparatus 10 includes an outer container and an inner LOX container spaced apart from the outer container. The space between the outer container and the inner container is preferably evacuated to at least a partial vacuum in order to minimize heat transfer to the LOX inside the inner container. The LOX capacity of inner LOX container is approximately point nine (0.9) pounds of LOX.

When LOX is withdrawn from the inner LOX container of the portable LOX delivery apparatus 10, it passes through the liquid withdrawal warming coil in which the LOX transforms to a gaseous phase. The liquid withdrawal warming coil warms the LOX by exposure to room temperature. Furthermore, an additional gas withdrawal warming coil may be utilized to further warm the gaseous oxygen before subsequent inhalation by an individual via cannula 63.

It can be appreciated that using a conventional LOX system 80, the freedom of travel of the user is limited by the amount of gas that is stored in portable LOX delivery apparatus 10. Once the supply in the portable LOX delivery apparatus is depleted, the user must return to the LOX source, i.e., stationary LOX storage canister 14 at his or her home, to refill the portable LOX delivery apparatus. Of course, the user can attempt to take the stationary LOX storage canister 14 with them, but this requires a vehicle adapted and sized so as to carry the stationary LOX storage canister.

Figure 5:
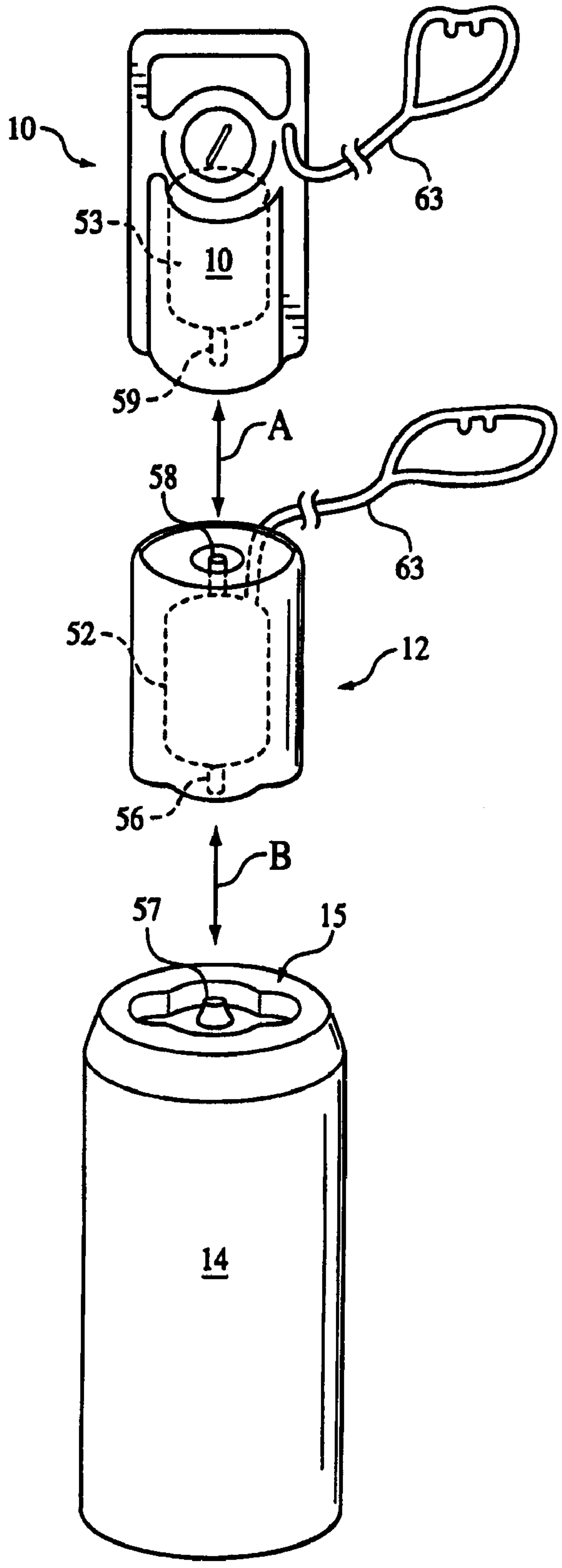
FIG. 5 schematically illustrates a LOX system of the present invention, including a portable liquid oxygen recharger adapted to interface with both a LOX storage tank and a LOX delivery apparatus according to principles of the present invention.

LOX system 5 of the present invention, which is shown in FIG. 5, provides an intermediate supply of LOX in portable LOX recharger 12. This extra LOX supply effectively increases the range of travel for the user, without requiring the user to carry the stationary LOX storage canister 14. Once the supply of LOX in portable LOX delivery apparatus 10 is depleted, the user can refill the portable LOX delivery apparatus from portable LOX recharger 12, so that he or she does not have to return to the stationary LOX storage canister. The relatively light weight of the portable LOX recharger mask makes is easy to carry and store, thereby improving the freedom, and, hence, quality of life of the user.

The present invention contemplates that providing the capability for the user to "breathe" off of portable LOX recharger 12 directly. This is shown in FIG. 5 by providing a nasal cannula 63 coupled to portable LOX recharger. Of course, tubing and a boil-off coil (not shown) would be needed to transition the LOX to a gaseous state for consumption by a user.

The present invention further contemplates that portable LOX recharger 12 includes one or more features that allow the user to monitor the amount of LOX remaining in the inner container. For example, a scale 82 (FIG. 3) can be provide to monitor the amount of LOX in inner container 52 based on the relative weight of the inner container. Of course, any technique for gauging the amount of LOX contained in the portable LOX recharger are contemplated by the present invention, such as floats, depth gauges, etc.

The present invention also contemplates providing sensors and alarms to warn of any malfunctions or other conditions of portable LOX recharger 12. For example, tilt meters and associated alarms and/or switches can be used to monitor the orientation of portable LOX recharger 12 and warn the user if an improper position is detected and/or disable the flow to or from the unit in such event. In addition, flow sensors, temperature sensors, pressure sensors, oxygen concentration sensors, and other monitoring devices can be provided. The present invention further contemplates providing a processor or other capability associated with portable LOX recharger 12 so that it can perform operations, such as self diagnostic functions, monitor the LOX level and provide refilling reminders, communicate information to or from an external source. To this end, a communication link (wireless or hardwired) can also be included to allow the portable LOX recharger 12 to communicate with an external device. An interface or other means can be used to communicate with the processor. Finally, the present invention contemplates providing handles, straps, wheels, rollers, or any other mechanism that allows the portable LOX recharger to be easily moved from one place to another by a typical user.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A portable liquid oxygen delivery system for an individual comprising:

a portable liquid oxygen delivery apparatus having a first interior adapted to contain a first quantity of liquid oxygen, wherein the portable liquid oxygen delivery apparatus is sufficiently lightweight for portability by an ambulatory patient, and wherein the portable liquid oxygen delivery apparatus includes a fill port adapted to receive liquid oxygen into the first interior, and a delivery port adapted to dispense liquid oxygen form the first interior; and a portable liquid oxygen recharger having a second interior adapted to store a second quantity of liquid oxygen that is greater than the first quantity and less than a third quantity contained in a stationary storage canister, wherein the portable liquid oxygen recharger is sufficiently lightweight for portability by an ambulatory patient, and wherein the portable liquid oxygen recharger includes an interface adapted to be coupled to the fill port of the portable liquid oxygen delivery apparatus enabling liquid oxygen to be delivered from the portable liquid oxygen recharger to the portable liquid oxygen delivery apparatus, such that a user is provided with a first quantity of liquid oxygen contained in the portable liquid oxygen delivery apparatus that is replenished from the second quantity of liquid oxygen from the portable liquid oxygen recharger without interfacing with the stationary storage canister.

2. The system of claim 1, wherein the portable liquid oxygen delivery apparatus has a storage capacity of at least 0.9 pounds, and the portable liquid oxygen recharger has a storage capacity of at least 1.9 pounds.

3. The system of claim 1, wherein the portable liquid oxygen recharger has a recharger fill port for receiving liquid oxygen from such a stationary storage canister.

4. The system of claim 3, wherein the interface and the recharger fill port are separate ports operatively coupled to the portable liquid oxygen recharger.

5. The system of claim 1, wherein the portable liquid oxygen recharger further comprise an automatic shutoff assembly adapted to reduce a loss of liquid oxygen when the portable liquid oxygen recharger receives liquid oxygen from such a stationary storage canister.

6. The system of claim 5, wherein the automatic shutoff assembly comprises:

a pressure release tube adapted to receive an internal pressure from the portable liquid oxygen recharger when the portable liquid oxygen recharger receives liquid oxygen from such a stationary storage canister;

a floating shutoff plug adapted to engage an opening defined in the pressure release tube, wherein the floating shutoff plug prevents the pressure release tube from communicating liquid oxygen from the portable liquid oxygen recharger responsive to the floating shutoff plug engaging the opening; and a floating shutoff plug holder adapted to position the floating shutoff plug at a predetermined distance from the opening.

7. The system of claim 6, wherein the pressure release tube comprises a pressure equalizing aperture for receiving a nominal amount of liquid oxygen from the portable liquid oxygen recharger when the floating shutoff plug engages the opening.

8. The system of claim 1, wherein the portable liquid oxygen recharger has a total weight less than eleven pounds when filled with liquid oxygen.

9. An intermediate liquid oxygen (LOX) source for a LOX delivery system including a portable liquid oxygen delivery apparatus and a stationary LOX canister, the intermediate LOX source comprising:

an outer recharger LOX container;

an inner recharger LOX container offset from the outer recharger LOX container, the inner recharger LOX container having an interior for storing LOX;

a fill port in communication with the inner recharger LOX container for receiving LOX from an external supply;

a discharge port in communication with the inner recharger LOX container for communicating LOX from the inner recharger LOX container interior to a portable medical delivery apparatus; and a fill vent in communication with the inner recharger LOX container interior, the fill vent having a first position that enables LOX to be received within the inner recharger LOX container interior, and a second position that inhibits LOX from being delivered to the inner recharger LOX container interior.

10. The intermediate LOX source of claim 9, further comprising an automatic shutoff assembly for reducing a loss of LOX received within the inner recharger LOX container interior when the fill vent is in the first position.

11. The intermediate LOX source of claim 10, wherein the automatic shutoff assembly comprises:

a pressure release tube in communication with the fill vent and the inner recharger LOX container interior for communicating internal pressure from the inner recharger LOX container interior to the fill vent;

a floating shutoff plug adapted to engage an opening defined in the pressure release tube, wherein the floating shutoff plug prevents the pressure release tube from communicating LOX from the inner recharger LOX container interior to the fill vent responsive to the floating shutoff plug engaging the opening; and a floating shutoff plug holder in communication with the opening and the floating shutoff plug, wherein the floating shutoff plug holder is adapted to position the floating shutoff plug a predetermined distance from the opening.

12. The intermediate LOX source of claim 11, wherein the pressure release tube includes a pressure equalizing aperture in communication with the fill vent and the inner recharger LOX container interior, where the pressure equalizing aperture communicates a nominal amount of received LOX from the inner recharger LOX container interior to the fill vent.

13. The intermediate LOX source of claim 12, wherein the pressure equalizing aperture equalizes a pressure of the inner recharger LOX container interior with a pressure of the outer recharger LOX container, and wherein the floating shutoff plug disengages from the opening responsive to the pressure of the inner recharger LOX container interior equaling the pressure of the outer recharger LOX container.

14. The intermediate LOX source of claim 9, further comprising a relief valve in communication with the inner recharger LOX container interior, wherein the relief valve is adapted to discharge LOX if a pressure level within the inner recharger LOX container interior exceeds a predetermined level when the fill vent is in the second position.

15. The intermediate LOX source of claim 9, wherein the intermediate LOX source has a LOX capacity of at least 1 pound.

16. The intermediate LOX source of claim 9, wherein the intermediate LOX source weighs less than 11 pounds when filled with LOX.

17. The intermediate LOX source of claim 9, further comprising a housing for enclosing the inner and the outer recharger LOX containers, and wherein an evacuated space exists between the inner and the outer recharger LOX containers.

18. The intermediate LOX source of claim 17, wherein the housing includes a first side and a second side, wherein the first side has a curved profile.

19. A liquid oxygen (LOX) delivery system comprising:

(a) a stationary canister adapted to contain a first quantity of LOX, wherein the stationary canister remains at a fixed location, wherein the stationary canister includes a LOX discharge port;

(b) a portable liquid oxygen recharger adapted to contain a second quantity of LOX that is less than the first quantity, wherein the portable liquid oxygen recharger is adapted to be carried by a user when filled with LOX, and wherein the portable liquid oxygen recharger includes (1) an inlet port adapted to be coupled to the LOX discharge port, and (2) an interface;

(c) a portable liquid oxygen delivery apparatus adapted to contain a third quantity of LOX that is less than the second quantity, wherein the portable liquid oxygen delivery apparatus is sufficiently lightweight so as to be carried by a user when filled with LOX, wherein the portable liquid oxygen delivery apparatus includes:

(1) a fill port adapted to LOX, (2) a delivery port adapted to dispense LOX, (3) vaporization system adapted to convert at least a portion the LOX in the portable liquid oxygen delivery apparatus to a breathable gas, and (4) a patient interface system adapted to communicate the gas to an airway of a patient, wherein the interface of the portable liquid oxygen recharger is adapted to be coupled to the fill port of the portable liquid oxygen delivery apparatus enabling the portable liquid oxygen delivery apparatus to be replenished with LOX without interfacing the portable liquid oxygen delivery apparatus with the stationary storage canister.

20. The system of claim 19, wherein the portable liquid oxygen delivery apparatus has a storage capacity of at least 0.9 pounds, and the portable liquid oxygen recharger has a storage capacity of at least 1.9 pounds.

21. The system of claim 19, wherein the portable liquid oxygen recharger further comprise an automatic shutoff assembly adapted to reduce a loss of LOX when the portable liquid oxygen recharger receives LOX from such a stationary storage canister.

22. The system of claim 19, wherein the portable liquid oxygen recharger has a total weight less than eleven pounds when filled with LOX.

* * * * *